Figure 1:
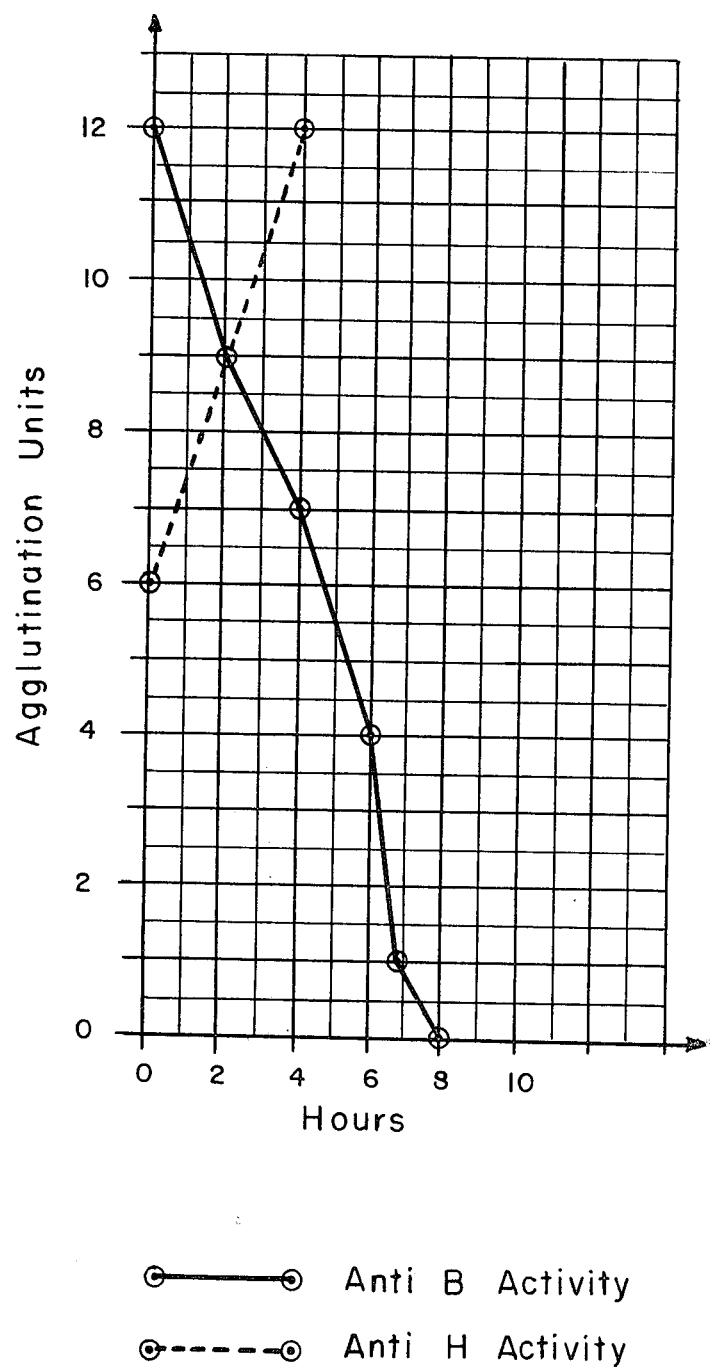

United States Patent [19]

Goldstein

[11] 4,330,619

[45] May 18, 1982

[54] ENZYMATIC CONVERSION OF RED CELLS FOR TRANSFUSION

[75] Inventor: Jack Goldstein, New York, N.Y.

[73] Assignee: New York Blood Center, Inc., New York, N.Y.

[21] Appl. No.: 177,972

[22] Filed: Aug. 14, 1980

[51] Int. Cl.$^3$ .................. A01N 1/02; A61K 35/14
[52] U.S. Cl. .................................... 435/2; 424/101
[58] Field of Search ........................ 435/2; 424/101

[56] References Cited

PUBLICATIONS

Harpaz et al–Arch. Biochem. & Biophys., vol. 170 (1975) pp. 676–683.

*Primary Examiner*—Sam Rosen

*Attorney, Agent, or Firm*—Sprung, Horn, Kramer & Woods

[57] ABSTRACT

A composition comprising type O erythrocyte free of $P_1$ antigenicity; a method of converting erythrocytes of the B antigen type to erythrocytes of the H-antigen type which comprises:

A. equilibrating said erythrocytes to a pH of 5.7–5.8;
B. thereafter contacting the so-equilibrated erythrocytes with an enzyme for a period sufficient to convert the B antigen in said erythrocytes to the H-antigen;
C. thereafter removing said enzyme from said erythrocytes and
D. re-equilibrating said erythrocytes to a pH of 7.2–7.4.

The specification discloses conversion of the B antigens in human and animal blood to the H antigen (O cells).

12 Claims, 2 Drawing Figures

FIG. I.

ENZYMATIC CONVERSION OF RED CELLS FOR TRANSFUSION

ACKNOWLEDGMENT

The Government has rights in this invention pursuant to Contract Number N00014-79-C-0242 awarded by the Department of the Navy.

BACKGROUND OF THE INVENTION

1. Field of the Invention

This invention relates to the conversion of blood types of B erythrocytes into type O cells to render for use in transfusion therapy. More especially, this invention relates to a process for the conversion of B erythrocytes into type O cells under conditions whereby the cells do not lose their cellular functions, are suitable for the adsorption and release of oxygen whereby the cells can be transfused in the manner of type O blood. This invention also relates to the products obtained by the conversion of such B erythrocytes into type O cells.

2. Discussion of Prior Art

As is well known in transfusion therapy, it is necessary to match the blood type of the recipient with the type of blood available in the blood bank. Thus, for instance, a recipient of type A blood can only be safely transfused with type A blood. The exception to this is type O blood, the erythrocytes of which can be safely transfused into type A, type B and type A,B recipients as well as O recipients.

In the operation of a blood bank or other facility which accumulates whole blood or at least the red cell component thereof it is necessary to maintain supplies of each type of blood. It has not heretofore been possible to maintain only O type blood because there is a paucity of O type donors. O type donor blood has therefore been used largely for O type recipients. On the other hand, a majority of donors have A, B or AB blood and there can exist from time to time, an excess of these types of blood. It has become desirable, therefore, to adjust the supply to the demand. Specifically, it has been desired to convert A, B or AB type blood to an O type blood type—a universal donor.

The ABO blood group system was the first to be discovered and is the one of greatest importance from the point of view of blood transfusion. Individuals of blood types A,B and O express A,B and H antigens respectively. These antigens are not only found on the red cells but on the surfaces of all endothelial and most epithelial cells as well. In addition, glycoproteins having A,B and H antigenicity are also found in the tissue fluids and secretions of those individuals who have the ability, inherited as a Mendelian dominant character, to secrete these blood group substances, or factors as they are termed.

While the blood group substances are glycoproteins, the A B H active material obtained from cell membranes appear to be only glycolipids. For a time it was thought that blood group active glycoproteins, as well as glycolipids were present on the surface of the red cells. However, recent studies have shown that the A B H blood group activity so far found associated with glycoproteins isolated from the cell membrane is an artifact resulting from the isolation procedure.

Considerable work has been done to determine the structures of the A B H determinants. It was found that the blood group specificity of the entire molecule, which may contain one or more carbohydrate chains, attached to a peptide backbone, is determined by the nature and linkage of those monosaccharides situated at the non-reducing ends of these chains. The most important sugar for each specificity, often referred to as the immuno-dominant or immuno-determinant sugar, was found to be as follows: for H antigen, fructose; for a antigen, N-acetyl-galactosamine; and for the type B antigen, galactose. More recently, studies with A B H active glycolipids obtained from erythrocyte cell membranes also show the presence of the same immunodominant sugars at the reducing ends of the carbohydrate chains, attached to adjacent sugars by the same linkages. The carbohydrate chains are, in turn, linked to the ceramide, which is imbedded in the lipid bi-layer of the membrane. The length of the carbohydrate moiety may vary and it may have either a straight or branched structure. Thus, far four variants of blood group active A glycolipid, two of B and three of H, have been isolated from the erythrocyte cell membrane.

Through these studies, it was theorized that one could convert a type A or type B antigen into a type H antigen, corresponding to a type O cell by removal of one of the monosaccharide groups pendent from the cell. Specifically, in the case of the B antigen, it was postulated that the galactose moiety of the type B antigen could be removed enzymatically whereby the type B antigen would be converted to a type H antigen. Flowers and collaborators (Harpaz, N., Flowers H. M. and Sharon, N. Arch. Biochem. Biophys. 170 676 (1975)) postulated that the terminal galactose moiety could be hydrolyzed away from B antigenic determinant of stroma obtained from B-type cells. See also Yatziv, S., and Flowers, H. M., Biochem. Biophys. Res. Commun. 45 514 (1971). Efforts for the removal of the terminal galactose moiety from the B-antigenic determinate of stroma and intact red cells were successful. However, where attempts were made to reproduce the procedures of the published literature it was observed that while the terminal galactose moiety was removed, that considerable hemolysis occurred with the red cells breaking down so that the resultant composition was not useful in transfusion therapy.

It is an object of this invention, therefore, to provide a process in which the terminal galactose moiety of the B-antigenic determinant of stroma from A and AB type cells can be removed while leaving the red cells intact so that the resultant composition can be used in transfusion therapy. Specifically, it is an object of this invention to convert B type cells to O type cells whereby the cells remain intact and undergo little if any hemolysis and the resultant composition can be employed in transfusion therapy.

SUMMARY OF THE INVENTION

The foregoing objects are attained, in accordance with this invention, by a process which comprises:

A. equilibrating said erythrocytes to a pH of 5.7–5.8;

B. thereafter, contacting the so-equilibrated erythrocytes with an enzyme for a period sufficient to convert the B antigen in said erythrocytes to the H-antigen;

C. removing said enzyme from said erythrocytes; and

D. re-equilibrating said erythrocytes to a pH of 7.2–7.4.

The O cells which are recovered as a result of this process are substantially free of terminally alpha linked galactose moiety which was present on the original B cells. This means not only a loss of B antigenicity but in testing the recovered O cells for its various antigens, it was observed that the new O cells are free of $P_1$ antigenicity. This distinguishes the synthesized O cells from naturally occurring O cells, the latter of which exhibit $P_1$ antigenicity in 79% of the caucasian population. It is also probable that in recovered O cells, terminally alpha linked galactose has been removed from a trihexosyl ceramide normally present in all erythrocytes thus further distinguishing these cells from those of natural origin.

In the procedure of the invention, α-galactosidase is employed as the enzyme. The same can be in a free enzymatic form or can be disposed on a support. The support can either be a soluble support such as dextran or polyethyleneglycol or can be an insoluble support such as cellulose, and cross linked polymers of acrylamide, dextran and agarose.

The realization of non-hemolyzed erythrocytes in the H-antigen type is effected by initial equilibration of the B erythrocytes in the absence of enzyme to a critical pH of 5.7 to 5.8. The equilibration is desirably effected using a citrate-phosphate buffer of pH 5.7 to 5.8 which contains citric acid in a concentration of 0.02–0.05 M in addition to dibasic sodium phosphate in a concentration of 0.05 to 0.10 M and sodium chloride in a concentration of 0.15 M.

The equilibration is normally effected by suspending the erythrocytes in the buffer solution for a period of at least 5 minutes, preferably no longer than 15 minutes. In accordance with the preferred mode of this invention, the buffer is removed from the erythrocytes and fresh buffer is added again allowing the contact to be for a period of at least 5 minutes and preferably no longer than 15 minutes. Desirably a third contact of the erythrocytes with another fresh aliquot or buffer is effected, this third contact also being for at least 5 minutes, and preferably no longer than 15 minutes.

While in vitro tests reflect that the total contact time of the buffer with the erythrocytes can be up to two hours, it is preferred for in vivo considerations that the contact time not exceed two hours, preferably no shorter than ½ hour and preferably no longer than one hour. It must be remembered that the objective is to convert the B antigen to the H antigen while leaving the cellular body intact so that when employed in transfusion therapy, the cells can perform their normal functions, especially the adsorption and release of oxygen.

It is another extremely important feature of the invention that the contact of the erythrocytes with the enzyme occur only after the cells have been equilibrated to 5.7–5.8. In other words, the erythrocytes are not initially contacted with enzyme while in admixture with a pH lowering substance (buffer).

The equilibration to 5.7–5.8 is effected at 20°–26° C. preferably at room temperature. Sub-atmospheric and super-atmospheric pressures are not required, atmospheric pressure being employed.

Once the erythrocytes have been equilibrated to 5.7–5.8, the enzymatic conversion of the B type antigen to the H type antigen becomes simplified. The enzymatic reaction is effected by the use of α-galactosidase in the free or supported form employing 40–350 enzyme units per 50–600 μl of cells. Preferably, the enzyme is present in an amount of 160–300 units per 250–600 μl of cells.

The enzymatic conversion is effected at 22°–28° C. preferably 25°–27° C. for 30–150 minutes, preferably 45–60 minutes.

As indicated above, the enzyme can be in the form of a free enzyme or in the form of a supported enzyme, the support being either a soluble or insoluble support. Dextran is a preferred soluble support, especially dextran of weight average in molecular weight 20,000 to 80,000. Another desirable soluble support is polyethyleneglycol of weight average in molecular weight 10,000 to 80,000. Solids (insoluble) supports include cross-linked dextrans, agarose and cellulose.

Following the enzyme treatment, the enzyme is removed from the erythrocytes and the erythrocytes are re-equilibrated to pH 7.2 to 7.4 by washing the same with a buffer and allowing to remain in contact with the buffer for 15–30' following the last wash. The washing is for the dual purpose of adjusting the pH to 7.2–7.4 and removing enzyme and free galactose. Washing solutions which can be employed include those containing the following buffer: phosphate buffered saline which contains a concentration of 0.01 M potassium phosphate in the ratio of seven parts dibasic salt to 3 parts monobasic and a concentration of 0.9% sodium chloride. The washing is effected for at least three times, preferably three to five times, at a temperature of 20° to 26° C., preferably room temperature. There is no required time of washing except that the washing should be performed until one can no longer detect the presence of enzyme in the wash solution.

Thereafter, the cells are in the H-antigen form and can be used for transfusion therapy. For purposes of use in transfusion, the cells are diluted with a physiologically acceptable medium. Physiologically acceptable mediums include: sterile isotonic saline solution consisting of 0.9% sodium chloride and sterile isotonic solution containing 0.2% dextrose. Generally speaking, the concentration of the cells in the medium is between 40% and 70%, preferably between 40% and 45%. These conditions are comparable to those used for transfusion of fresh and frozen-thawed packed erythrocytes. The cells of the invention can be transfused in the same manner as known packed cells are transfused.

The converted O cells (H antigenicity), as revealed by in vitro studies of gibbon erythrocytes exhibit normal osmotic fragility patterns and retain normal membrane cholesterol and acetylcholinesterase levels—which confirm the absence of hemolysis and membrane damage as a result of the enzymatic process.

Cellular metabolic studies have indicated that adenosine-5'-triphosphates (ATP) content remain above 90% and 2,3-diphosphoglyceric acid (2,3 DPG) levels are 80–90% after treatment. This allows for maintenance of cell shape and for normal oxygen-binding and exchange.

The buffer and incubation conditions employed in accordance with the method provide a product at which there is essentially no change in ATP levels and about a 90% or more retention of 2,3 DPG for up to 3 hours of incubation. Human cell values obtained thus far for 3 hour treatments, including incubation and α-galactosidase, are on the order of 90% or more for ATP as found for the gibbon but exhibited a 60–90% range for 2,3 DPG, the lower value found when citrate is included in the treatment buffer.

Gibbon erythrocytes labeled with 51 Cr and subjected to enzymatic treatment conditions exhibit normal in vivo survival rates. This is also true when the enzyme is support i.e. is in the form of an enzyme dextran conjugate. In vitro studies show no antigenicity to have developed as a result of enzyme modification since antibody formation could not be detected even after more than one injection. Similarly, recipient animals have not developed detectable antibody either to free enzyme or to enzyme-dextran conjugate.

By using α-galactosidase as the enzyme, there was obtained a complete conversion of B cells to H activity. The time needed for this conversion is enzyme dependent and can be reduced by increasing amounts of enzyme. Fragility studies of the treated cells demonstrate that the treatment conditions do not produce any significant increase in susceptibility of these cells to osmotic shock. Inasmuch as older cells are more susceptible to osmotic lysis, these in vitro studies suggest that no induced premature aging of the converted cells has been effected. This is supported by microscopic examination of these cells which reveal them to be free of gross morphological abnormalities and to be capable of spherocyte discocyte interconversion. 3-membrane components, the Rh and M and N antigens and sialic acid show no gross changes between the original B cells and the converted H cells, whereas expression of the $P_1$ antigen, which, too, contains a terminal galactose residue in α-linkage is completely lost following enzyme treatment. Also, when type AB cells are converted to AH with this enzyme, there is no change in the levels of A activity of the cells and A and O (H) cells have been found to have their activities unaffected by the enzyme. Converted cells were checked with autologous plasma and do not show any panagglutination. As a further indication of the specificity of the enzyme, the only sugar which could be found to have been released in significant amounts following treatment of the B cells with the enzyme is that sugar which one expects, galactose. As a further indication that the enzymes preparations contaminating proteins were non-reactive with the red-cell membrane, acetylcholinesterase activity was unaffected by enzymatic treatment.

It has been additionally found that the conversion is especially effective when the α-galactosidase is employed in the form of a supported enzyme. Preferably, the support is a soluble support and most preferably it is a dextran of the molecular weight 20,000 to 80,000. The enzyme can be attached to the soluble support using cyanogen bromide as a covalent linking agent. However, in order to separate the enzyme dextran conjugate from unbound material, it was found necessary to subject the crude enzyme preparation to a simple purification procedure using Sephadex G-100 gel filtration prior to binding dextran. Purification conditions permit the use of a product of covalently bound α-galactosidase on dextrose or other soluble support which is completely free of unbound material. The enzyme-soluble support conjugate e.g. enzyme dextran conjugate has the same specificity and ability for removal of the B determinant from the surface of the red cells as the free enzyme preparation and can be reused and stored without loss of activity. The use of such a conjugate is desired since they can be used repeatedly and their use is not characterized by side reactions due to impurities in starting enzyme material as is the case when free enzyme is employed. These impurities can be more readily controlled making it possible to use only partially purified preparations for coupling. Using the synthetic substrate p-nitrophenyl α-galactoside, kinetic properties, thermal stability and pH optimal of the enzyme conjugate were compared with those of free enzymes. The conjugate is Km, Ks, KI, Vmax, optimal substrate connections and optimal pH are all lower than free enzyme while its resistance to thermal inactivation is greater.

Immobilized enzymes can be more readily separated from their substrates to minimize the possibility that some of the glycosidase molecules or contaminating proteins of free enzyme preparations will bind irreversibly to the cell structure, thus introducing potential antibody-producing substances or be removable only under stringent washing conditions likely to damage the membrane of the cell.

Of the α-galactosidase preparations which are commercially available, it is preferred to employ that product sold by Boehringer-Mannheim Biochemicals. It is an α-galactosidase (α-D-galactoside galactohydrolase EG 3.2.1.22) and is prepared from green coffee beans by the manufacturer's own procedure. It has a specific activity of ten units per mg of protein determined by hydrolysis of p-Nitrophenol α-D Galactoside. The 5 exoglycosidase contaminants this product is reported to contain at levels less than 0.05% for each are N-acetyl-β-D-glucosaminidase, β-galactosidase, β-glucosidase, α-glucosidase and α-mannosidase. Using this enzyme preparation without further purification complete conversion of B cells to H activity and $A_1B$ and $A_2B$ cells to their respective AH counterparts are measured by a hemagglutination assay and release of galactose. The time needed for this conversion is again enzymatically dependent and can be reduced by increasing amounts of enzymes as for example, in the case of B cells (0.1 ml) from 13 hours (8 units) to 7.8 hours (16 units) to 4 hours (32 units). The results of the typical enzymatic treatment of B cells si shown in FIG. 1. The treatment conditions include: citrate-phosphate buffer pH 5.8 (0.02 m citric acid and 0.06 m dibasic sodium phosphate) in isotonic saline, incubation at 26° C. and the use of a rotary mixer at slow speed.

Figure 2:
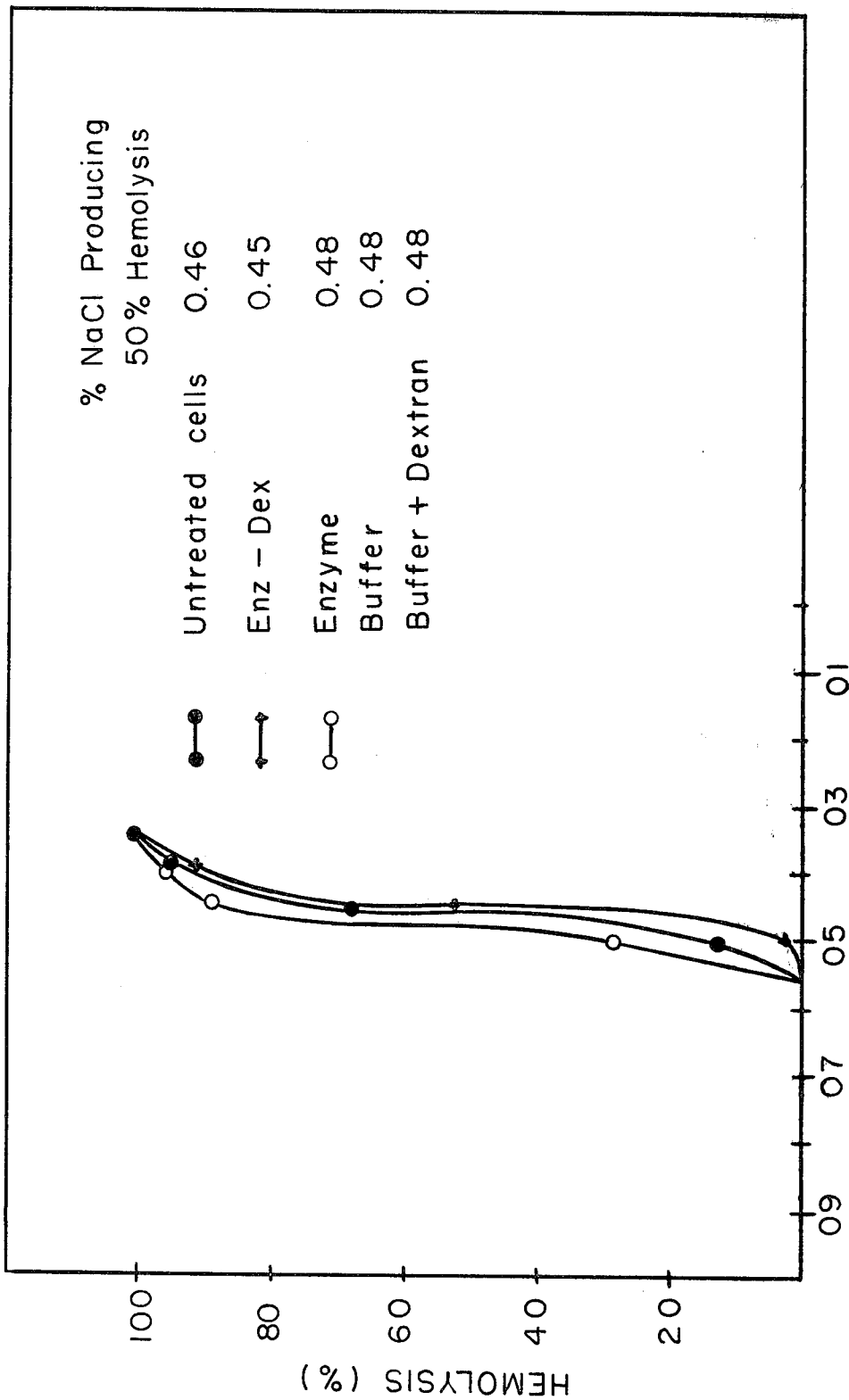

Fragility studies of the enzymatically treated cells and appropriate controls as shown in FIG. 2 demonstrate that the treatment conditions do not produce any significant increase in susceptibility of these cells to osmatic shock, i.e. the 50% homolysis times are quite close, suggesting that no meaningful induction of premature agent of the converted cells has occurred.

EXAMPLES

In order to more fully illustrate the nature of the invention and the manner of practicing the same, the following examples are presented.

EXAMPLE 1

Whole blood was obtained containing erythrocytes of the B antigen type. The plasma was removed from the whole cells after which the white cells were removed by aspiration in an isotonic saline solution. The red cells were washed three times with an isotonic saline solution.

Thereafter, the red cells were suspended in a buffered solution at pH 5.8 and washed three times to ensure pH equilibrium. The red cells were washed three times with isotonic saline and then three times with isotonic phosphatecitrate buffer pH 5.8.

0.1 ml of packed B+ erythrocytes were suspended in isotonic phosphate-citrate buffer pH 5.8 containing 16 unites of α-galactosidase in a final volume of 2 ml. Incubation was carried out at 26° C. in a rotary mixer rotating at 2-5 rpm. 0.2 ml aliquots were removed at various times, the cells centrifuged and washed with isotonic saline and tested by hemagglutination assay for anti-B and anti-H activity using human anti-B antisera and the H specific lectin obtained from Ulex europeus.

The results are shown in FIG. 1. Please note that a score of 12 is obtained with untreated B and H cells. This top score of H activity is reached with the treated B cells before complete removal of all reacted B antigenic determinants indicating sufficient H antigenic sites have been uncovered to react maximally with the Ulex reagent.

Osmotic fragility measurements or erythrocytes following various buffer and enzymatic treatments was also conducted. Following the various indicated treatments (FIG. 2), the cells were centrifuged and washed with isotonic 0.01 M potassium phosphate buffer pH 7.4 and allowed to remain for two hours in the same buffer after which 10 μl aliquots were incubated at 37° C. for 30 minutes in the indicated concentration of sodium chloride, centrifuged, and amounts of hemolysis determined by adding cyanmet reagent to the supernatant to measure the amount of hemoglobin released.

EXAMPLE 2

In the manner of Example 1, human erythrocytes exhibiting B antigenicity were incubated with
α-galactosidase
α-galactosidase-dextran conjugate
α-galactosidase + dextran
buffer.

All enzyme treatments were found to convert the B cells into cells exhibiting H antigenicity equivalent to those found in type O cells. α-galactosidase-dextran removed B antigenicity at a faster rate than the free enzyme. Addition of dextran to free enzyme increased the rate to that of the enzyme conjugate indicating that dextran alone can have a facilitating effect on the enzyme interaction of the surface of the red cell. There is set forth below Table I which shows the anti-B hemagglutination scores of the untreated red cells against the various treating agents.

TABLE 1

RATE OF LOSS OF B ANTIGENIC ACTIVITY FROM ENZYME-TREATED HUMAN RED CELLS

| | ANTI-B HEMAGGLUTINATION SCORE AT: | | | | |
|---|---|---|---|---|---|
| 100 μl Type B Erythrocytes Incubated with | 15' | 30' | 45' | 60' | 70' |
| 80 units α-galactosidase | 12 | 11 | 9 | 4 | 0 |
| 80 units α-galactosidase-dextran conjugate | 12 | 3 | 0 | 0 | 0 |
| 80 units α-galactosidase plus dextran | 12 | 2 | 0 | 0 | 0 |
| Buffer | 12 | 12 | 12 | 12 | 12 |

Table 2 set forth below compares the ATP and 2,3-DPG levels of treated cells verus untreated cells after treatment with the indicated treating agents. The buffer used is the same buffer employed to generate the data set forth in Table 1 above, i.e. the phosphate citrate buffer employed in Example 1.

TABLE 2

ERYTHROCYTE ADENOSINE 5' TRIPHOSPHATE AND 2,3-DIPHOSPHOGLYCERIC ACID LEVELS FOLLOWING TREATMENT

| | | % OF UNTREATED CELLS | |
|---|---|---|---|
| TREATMENT CONDITIONS | | ATP | 2,3-DPG |
| GIBBON | | | |
| BUFFER | 1 HR. | 89 | 77 |
| α-GALACTOSIDASE | 1 HR | 91 | 73 |
| DEXTRAN 15% | 1 HR | 88 | 80 |
| HUMAN | | | |
| BUFFER | 1 HR | 101 | 86 |
| | 2 HR | 101 | 75 |
| | 3 HR | 101 | 73 |
| | 4 HR | 99 | 60 |
| | 5 HR | 99 | 51 |
| | 6 HR | 109 | 39 |
| α-GALACTOSIDASE | 1 HR | 92 | 91 |
| DEXTRAN 15% | 1 HR | 105 | 84 |
| DEXTRAN 30% | 1 HR | 104 | 90 |
| α-GALACTOSIDASE-DEXTRAN 15% | 1 HR | 100 | 87 |
| α-GALACTOSIDASE-DEXTRAN 30% | 1 HR | 99 | 90 |

A 1-hour treatment produced a slight decrease in 2,3 DPG level in given cells but did not essentially alter ATP and 2,3 DPG levels in human cells.

Neither free enzyme nor enzyme-dextran conjugate significantly changed ATP or 2,3 DPG levels.

What is claimed is:

1. A method of converting erythrocytes of the B or A,B antigen type to erythrocytes of the H-antigen type which comprises:
    A. equilibrating said erythrocytes to a pH of 5.7–5.8;
    B. thereafter contacting the so-equilibrated erythrocytes with α-galactosidase for a period sufficient to convert the B antigen in said erythrocytes to the H-antigen; and
    C. thereafter removing said α-galactosidase from said erythrocytes and
    D. re-equilibrating said erythrocytes to a pH of 7.2–7.4.

2. A process according to claim 1, wherein said α-galactosidase is in the free enzyme form.

3. A process according to claim 1, wherein said α-galactosidase is in a supported form.

4. A process according to claim 3, wherein the support for said α-galactosidase is a soluble support.

5. A process according to claim 4, wherein said soluble support is selected from the group consisting of dextran and polyethylene glycol.

6. A process according to claim 3, wherein said support is an insoluble support.

7. A process according to claim 6, wherein said insoluble support is selected from the group consisting of agarose and cellulose.

8. A process according to claim 1, wherein the equilibration of the erythrocyte to a pH 5.7–5.8 is effective at 20° to 26° C. with a buffer.

9. A process according to claim 8, wherein said buffer is a citrate-phosphate buffer.

10. A process according to claim 9, wherein said α-galactosidase is present in an amount of 100 to 350 enzyme units per 80–600 microliters of cells and the treatment with the α-galactosidase is effected at 22 to 28° C. for 30–150 minutes.

11. A process according to claim 10, wherein the re-equilibration of the so-contacted erythrocytes is effected over a period of time of 15 to 30 minutes and for a period of time sufficient to remove α-galactosidase from the so-treated erythrocytes.

12. A process according to claim 1 wherein said α-galactosidase is one derived from a green coffee bean.

* * * * *